United States Patent [19]
Stoltefuss et al.

[11] Patent Number: 5,225,558
[45] Date of Patent: Jul. 6, 1993

[54] 2-AMINO-5-CYANO-1,4-DIHYDROPYRIDINES, AND THEIR USE IN MEDICAMENTS

[75] Inventors: Jürgen Stoltefuss, Haan; Siegfried Goldmann; Alexander Straub, both of Wuppertal; Horst Böshagen, Haan; Martin Bechem, Wuppertal; Rainer Gross, Wuppertal; Siegbert Hebisch, Wuppertal; Joachim Hütter, Wuppertal; Howard-Paul Rounding, Wuppertal, all of Fed. Rep. of Germany

[73] Assignee: Bayer Aktiengesellschaft, Leverkusen, Fed. Rep. of Germany

[21] Appl. No.: 886,644

[22] Filed: May 20, 1992

[30] Foreign Application Priority Data

May 30, 1991 [DE] Fed. Rep. of Germany ....... 4117750

[51] Int. Cl.$^5$ .................. C07D 401/04; A61K 31/44
[52] U.S. Cl. ................................................. 546/167
[58] Field of Search ......................... 546/167; 514/314

[56] References Cited
U.S. PATENT DOCUMENTS

| | | | |
|---|---|---|---|
| 2,359,329 | 10/1944 | Phillips et al. | 546/167 |
| 3,862,162 | 1/1975 | Meyer et al. | 260/295 R |
| 3,996,234 | 12/1976 | Bossert et al. | 546/167 |
| 4,001,250 | 1/1977 | Lantzsch et al. | 260/293.52 |
| 4,001,258 | 1/1977 | Meyer et al. | 546/167 |
| 4,532,248 | 7/1985 | Franckowiak et al. | 514/302 |
| 5,100,900 | 3/1992 | Stoltefuss et al. | 546/167 |

FOREIGN PATENT DOCUMENTS

| | | |
|---|---|---|
| 0026317 | 4/1981 | European Pat. Off. |
| 0071819 | 2/1983 | European Pat. Off. |
| 0073997 | 3/1983 | European Pat. Off. |
| 0452712 | 10/1991 | European Pat. Off. |
| 2623170 | 12/1977 | Fed. Rep. of Germany |
| 2658804 | 7/1978 | Fed. Rep. of Germany |
| 3015219 | 10/1981 | Fed. Rep. of Germany |

OTHER PUBLICATIONS

Journal of the Chemical Society, 1946, pp. 884–888.
Liebigs Ann. Chem. 1977, 1895–1908.
J. Heterocyclic Chem., 26, 1575 (1989).
Chem. Pharm. Bull., vol. 20, No. 10, pp. 2123–2127 (1972).
"Neuartige Kondensationsreaktionen . . . ", C. H. Eugster et al, volumen XLVI, Fasciculus II (1963)–No. 56057.
J. Physiol. (1965), 180, pp. 529–541.
J. Heterocyclic Chemistry, vol. 6, No. 2, Apr. 1969, pp. 243–245.

*Primary Examiner*—David B. Springer
*Attorney, Agent, or Firm*—Sprung Horn Kramer & Woods

[57] ABSTRACT

The present invention relates to new 2-amino-5-cyano-4-quinoline-1,4-dihydropyridines, processes for their preparation and their use in medicaments, in particular in agents for the treatment of cardiovascular diseases.

7 Claims, No Drawings

2-AMINO-5-CYANO-1,4-DIHYDROPYRIDINES, AND THEIR USE IN MEDICAMENTS

The present invention relates to new 2-amino-5-cyano-4-quinoline-1,4-dihydropyridines, processes for their preparation and their use in medicaments, in particular in agents for the treatment of cardiovascular diseases It is already known that some 2- and 6-amino-3,4-dihydropyridines also have a lipid absorption-inhibiting action, in addition to an antiarrhythmic action [compare EP 73,997].

2-Amino-1,4-dihydropyridines have furthermore been described, in some cases also with a vasodilatory and antihypertensive action [compare, for example, DE 2,242,786].

Knowing these properties of dihydropyridines, it was not foreseeable that the compounds according to the invention would have a contraction force-intensifying action which is positively inotropic on the cardiac muscle, coupled with a largely vasoneutral behaviour.

Some of the compounds of the formula (I) according to the invention fall under the general claim in EP 71,819, but without a concrete substance representative being mentioned therein.

The present invention relates to 2-amino-5-cyano-4-quinoline-1,4-dihydropyridines of the general formula (I)

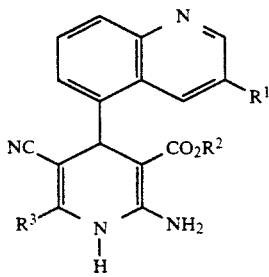

in which
$R^1$ represents aryl having 6 to 10 carbon atoms, which is optionally substituted up to 3 times, in an identical or different manner, by halogen, nitro, cyano, trifluoromethyl, trifluoromethoxy or trifluoromethylthio, or by straight-chain or branched alkyl having up to 8 carbon atoms, which can in turn be substituted by aryl having 6 to 10 carbon atoms, or is substituted by straight-chain or branched alkoxy or alkoxycarbonyl having in each case up to 8 carbon atoms, carboxyl or amino, or by a group of the formula $-NR^4R^5$, wherein $R^4$ and $R^5$ are identical or different and denote straight-chain or branched alkyl having up to 8 carbon atoms, phenyl or benzyl, or represents thienyl,
$R^2$ represents hydrogen, or represents cycloalkyl having 5 to 8 carbon atoms, or represents straight-chain or branched alkyl, alkenyl, alkadienyl or alkinyl having in each case up to 10 carbon atoms, which are optionally substituted once or twice, in an identical or different manner, by straight-chain or branched alkylthio, alkoxy, alkoxycarbonyl, acyl or acyloxy having in each case up to 8 carbon atoms, or by cycloalkyl having 3 to 8 carbon atoms, phenoxy or phenyl, it being possible for the latter in turn to be substituted up to twice, in an identical or different manner, by halogen or by straight-chain or branched alkyl or alkoxy having in each case up to 6 carbon atoms, or are substituted by the group $-NR^4R^5$, wherein $R^4$ and $R^5$ have the abovementioned meaning, and
$R^3$ represents hydrogen or straight-chain or branched alkyl having up to 8 carbon atoms,
and physiologically acceptable salts thereof.

Physiologically acceptable salts are salts of the compounds according to the invention with inorganic or organic acids. Salts with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid, are preferred.

The compounds according to the invention exist in stereoisomeric forms which are either mirror images (enantiomers) or not mirror images (diastereomers). The invention relates both to the antipodes and to the racemic forms, as well as to the diastereomer mixtures. The racemic forms, like the diastereomers, can be separated into the stereoisomerically uniform constituents in a known manner (compare E. L. Eliel, Stereochemistry of Carbon Compounds, McGraw Hill, 1962).

Preferred compounds are those of the general formula (I) in which
$R^1$ represents phenyl, which is optionally substituted up to 3 times, in an identical or different manner, by halogen, nitro, cyano or trifluoromethyl, or by straight-chain or branched alkyl or alkoxy having in each case up to 6 carbon atoms, benzyl or by a group of the formula $-NR^4R^5$, wherein $R^4$ and $R^5$ are identical or different and denote hydrogen, straight-chain or branched alkyl having up to 6 carbon atoms, phenyl or benzyl, or represents thienyl,
$R^2$ represents hydrogen, or represents cyclopentyl or cyclohexyl, or represents straight-chain or branched alkyl or alkenyl having in each case up to 10 carbon atoms, which are optionally substituted by halogen, hydroxyl, carboxyl or cyano, or by straight-chain or branched alkylthio, alkoxycarbonyl, alkoxy, acyl or acyloxy having in each case up to 6 carbon atoms, cyclopropyl, cyclopentyl, cyclohexyl, phenoxy or phenyl, it being possible for the last two to be substituted by halogen, methyl, methoxy or ethoxy, or are substituted by the group $-NR^4R^5$, wherein $R^4$ and $R^5$ have the abovementioned meaning, and
$R^3$ represents hydrogen or straight-chain or branched alkyl having up to 6 carbon atoms,
and physiologically acceptable salts thereof.

Particularly preferred compounds are those of the general formula (I) in which
$R^1$ represents phenyl, which is optionally substituted up to twice, in an identical or different manner, by fluorine, chlorine, nitro or trifluoromethyl, or by straight-chain or branched alkyl or alkoxy having in each case up to 4 carbon atoms, or by a group of the formula $-NR^4R^5$, wherein $R^4$ and $R^5$ are identical or different and denote hydrogen or straight-chain or branched alkyl having up to 4 carbon atoms, phenyl or benzyl, or represents thienyl,
$R^2$ represents hydrogen, or represents cyclopentyl, or represents straight-chain or branched alkyl having up to 8 carbon atoms, which is optionally substituted by fluorine, chlorine, hydroxyl, carboxyl or cyano, or by straight-chain or branched alkoxycarbonyl, alkoxy or acyloxy having in each case up to 4 carbon atoms, phenyl, phenoxy, cyclopropyl, cyclopentyl or cyclohexyl, or by the group —NR⁴R⁵, wherein R⁴ and R⁵ have the abovementioned meaning, and R³ represents hydrogen, or represents straight-chain or branched alkyl having up to 4 carbon atoms, and physiologically acceptable salts thereof.

The preparation of the compounds of the general formula (I) according to the invention is characterised in that

[A] either aldehydes of the general formula (II)

(II)

in which R¹ has the abovementioned meaning, are reacted directly with compounds of the general formula (III)

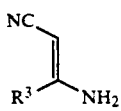
(III)

in which R³ has the abovementioned meaning, and compounds of the tautomeric formulae (IV) or (IVa)

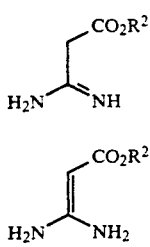
(IV)

(IVa)

in which R² has the abovementioned meaning, in inert solvents at temperatures between 10° C. and 150° C.,

[B] or ylidene compounds of the general formula (V)

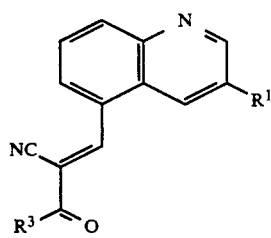
(V)

in which R¹ and R³ have the abovementioned meaning, are reacted with compounds of the general formula (VI) or (VIa)

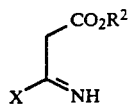
(VI)

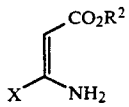
(VIa)

in which

R² has the abovementioned meaning and

X represents the amino group or the group OR⁶, wherein R⁶ represents C₁-C₄-alkyl, if appropriate in the presence of inert organic solvents at temperatures of 10° C. to 150° C., ammonium salts, such as ammonium acetate being added in the case where X represents the group OR⁶.

In the case of the pure enantiomers, either the diastereomer mixture formed from the particular compounds of the general formula (I) in which R² represents a defined chiral radical is first separated and then converted into the corresponding carboxylic acids (R²=H), which are esterified in a final step, or the particular diastereomers are transesterified directly with the corresponding alcohols, in particular in the form of the alcoholates.

The processes according to the invention can be illustrated by way of example by the following equation:

[A]

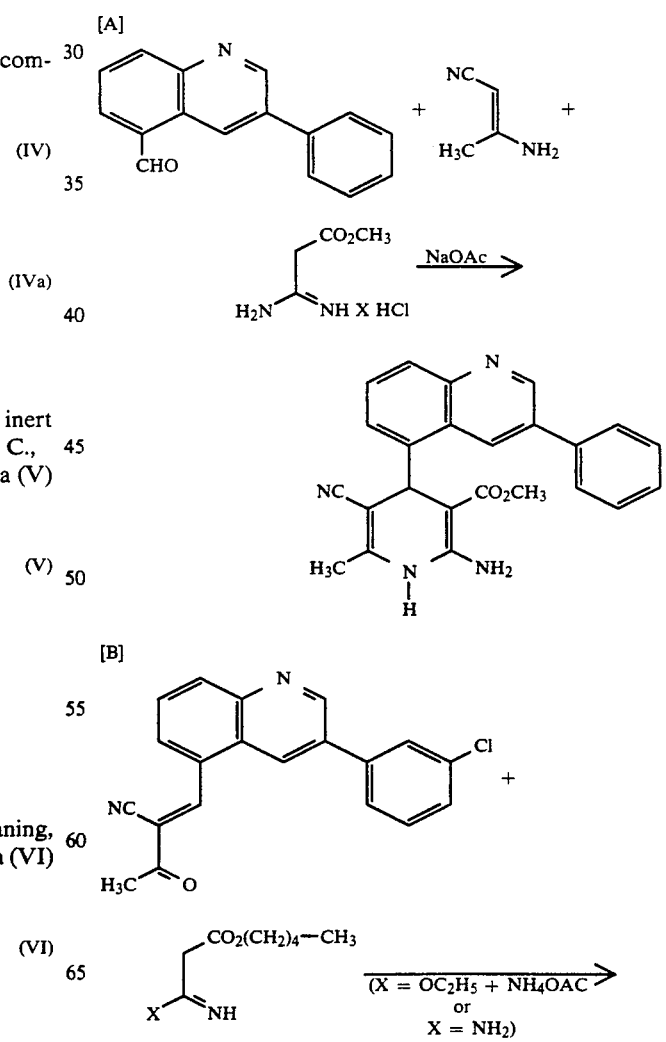

[B]

-continued

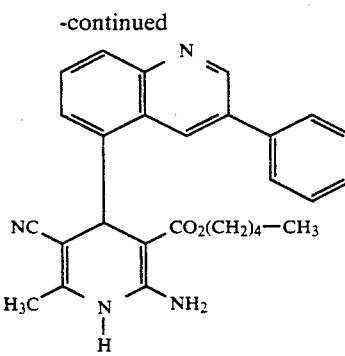

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric acid triamide or dimethylformamide, or acetic acid, alkyl acetates or halogenated hydrocarbons, such as methylene chloride or carbon tetrachloride, or hydrocarbons, such as benzene or toluene. It is also possible to use mixtures of the solvents mentioned Methanol, isopropanol, ethanol and n-propanol, acetonitrile or tetrahydrofuran are preferred, depending on the particular process variant [A] or [B].

The reaction temperatures can be varied within a relatively wide range. The reaction is in general carried out between +10° C. and +150° C., preferably between +20° C. and 100° C., in particular at the boiling point of the particular solvent.

The reaction can be carried out under normal pressure, but also under increased or reduced pressure (for example 0.5 to 3 bar). It is in general carried out under normal pressure.

Suitable chiral ester radicals are all the esters of enantiomerically pure alcohols, such as, for example, 2-butanol, 1-phenylethanol, lactic acid, lactic acid esters, mandelic acid, mandelic acid esters, 2-aminoalcohols, sugar derivatives, hydroxyamino acid derivatives and many other enantiomerically pure alcohols.

The diastereomers are in general separated either by fractional crystallisation, by column chromatography or by Craig partition. Which process is the optimum must be decided from case to case, and it is sometimes also advantageous to use combinations of the individual processes. Separation by crystallisation or Craig partition or a combination of the two processes is particularly suitable.

The compounds of the general formula (II) are known in some cases and can be prepared by customary methods, for example by oxidising the corresponding alkyl- or hydroxyalkyl-quinolines or reducing the corresponding carboxyquinolines (compare also German Offenlegungsschrift 4,011,105).

Alternatively, 4-amino-3-hydroxyphthalide, which is obtained by customary hydrogenation of 4-nitro-3-hydroxyphthalide which is known from the literature [T. Watanabe et al., Chem. Pharm. Bull. 20 (10), 2123-2127 (1970)] in the presence of a catalyst, preferably with palladium/barium sulphate, can also be reacted with compounds of the general formula $R^1$—$CH_2$—CHO, some of which are known [compare, for example, Beilstein 7, 292], to give compounds of the general formula (II) via the corresponding carboxylic acids.

The compounds of the general formula (III), (IV) and (IVa) are known per se or can be prepared by methods known from the literature [compare J. Heterocycl. Chem. 6, 1575 (1989); and Liebigs Ann. Chem. 1977, 1895-1908].

The ylidene compounds of the general formula (V) are new and can be prepared by a process in which compounds of the general formula (VII)

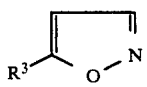

(VII)

in which
$R^3$ has the abovementioned meaning, are converted with alkali metal hydroxides or alkali metal alcoholates into the alkali metal salts of the compounds of the general formula (VIII)

$$R^3—CO—CH_2—CN \qquad (VIII)$$

in which
$R^3$ has the abovementioned meaning, and these are reacted, either in situ or after isolation, with aldehydes of the general formula (II) in one of the abovementioned inert solvents, preferably in alcohols, ethyl acetate, methylene chloride, acetonitrile, chloroform or ethers, with the addition of acid, preferably acetic acid, and if appropriate in the presence of a catalyst, for example piperidine acetate, at temperatures between 0° C. and 150° C., preferably between 20° C. and 110° C.

The compounds of the general formula (VII) are also known in most cases, or can be prepared by a customary method [compare Helv. Chim. Acta, Volume XLVU, Fasciculens II (1963), No. 56-57, pages 543-551].

The compounds of the general formula (VIII) are also known or can be prepared by methods known from the literature.

The compounds according to the invention exhibit an unforeseeable, useful pharmacological action spectrum. They influence the contraction force of the heart and the tone of the smooth muscle. Preferably, they exhibit a positively inotropic action. They can therefore be employed in medicaments for influencing pathologically changed blood pressure, as coronary therapeutics and for the treatment of cardiac insufficiency. They can moreover be used for the treatment of disturbances in cardiac rhythm, for reducing blood sugar, for detumescing mucosa and for influencing the salt and fluid balance.

The cardiovascular actions were found on the isolated perfused heart of the guineapig. The hearts of guineapigs weighing 250 to 350 g are used for this. The animals are sacrificed with a blow on the head, the thorax is opened and a metal cannula is inserted into the exposed aorta. The heart is removed from the thorax with the lung and connected via an aorta cannula to the perfusion apparatus with the perfusion running. The lungs are removed at the lung roots, and the perfusion medium used is a Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of NaH- CO₃ and 0.013 mmol/l of Na₂EDTA), the CaCl₂ content of which is 1.2 mmol/l. 10 mmol/l of glucose are added as the energy-supplying substrate. Before the perfusion, the solution is filtered free from particles. The solution is gassed with carbogen (95% of $O_2$, 5% of $CO_2$) to maintain the pH of 7.4. The hearts are perfused at a constant flow rate (10 ml/minute) at 32° C. by means of a roller squeeze pump.

To measure the cardiac function, a latex balloon filled with liquid and connected to a pressure transducer via a column of liquid is inserted through the left atrium into the left ventricle, and the isovolumetric contractions are recorded on a high-speed recorder (Opie, L., J. Physiol. 180 (1965), 529-541). The perfusion pressure is recorded by means of a pressure transducer connected to the perfusion system upstream of the heart. Under these conditions, a reduction in the perfusion pressure indicates coronary dilation and an increase or decrease in the left ventricular contraction amplitude indicates a reduction or an increase in cardiac contractility. The compounds according to the invention are perfused into the perfusion system in suitable dilutions shortly upstream of the isolated heart.

Substance effects on the contraction amplitude of isolated guineapig atria at an active compound concentration of 10.4 g/l.

| Example No. | Contraction force (% of control) |
|---|---|
| 6 | +14 |
| 7 | +103 |
| 13 | +21 |
| 14 | +43 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, it being possible, for example in the case where water is used as a diluent, for organic solvents to be used as auxiliary solvents if appropriate.

Administration takes place in the customary manner, preferably orally or parenterally, in particular perlingually or intravenously.

In general it has proved advantageous in the case of intravenous administration to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may be necessary, if appropriate, to deviate from the amounts mentioned, and in particular to do so as a function of the body weight or type of administration route, the behaviour of the individual towards the medicament, the nature of the formulation thereof and the time or interval at which administration takes place. Thus in some cases it may be sufficient to manage with less than the abovementioned minimum amount, while in other cases the upper limit mentioned must be exceeded. Where relatively large amounts are administered, it may be advisable to distribute these into several individual doses over the day.

STARTING COMPOUND

Example I 1-(3-Phenylquinol-5-ylidene)-3-oxo-butyronitrile

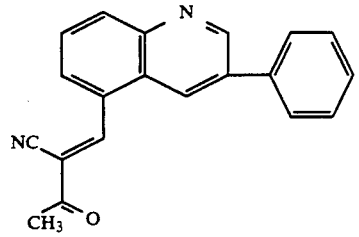

15.45 g (66.3 mmol) of 3-phenyl-quinoline-5-aldehyde are boiled in 420 ml of methylene chloride with 6.97 g (66.4 mmol) of 3-oxo-butyronitrile sodium salt (obtained by dissolving 5-methylisoxazole in the equivalent amount of sodium methylate solution and concentrating the solution), 4.34 ml of acetic acid and 0.66 ml of piperidine for 24 hours, using a water separator. The mixture is cooled, washed twice with water, filtered to remove a little by-product which has precipitated, and concentrated. The desired product crystallises on stirring with ethanol. 12.7 g of yellow crystals of melting point 142° C. to 144° C. are obtained.

Example 1 (Process B)

(S)-(1-Methoxycarbonyl)-ethyl 2-amino-1,4-dihydropyridine-5-cyano-6-methyl-4-(3-phenylquinolin-5-yl)-3-carboxylate

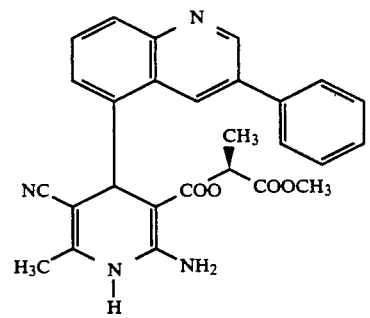

Method A 2,5 g (8.4 mmol) of 1-(3-phenylquinol-5-ylidene)-3-oxobutyronitrile are boiled overnight in 15 ml of isopropanol with 2.2 g (10.1 mmol) of (S)-(1-methoxycarbonyl)-ethyl 3-imino-3-ethoxy-acetate and 1.43 g (18.44 mmol) of ammonium acetate. The mixture is concentrated, the residue is taken up in ethyl acetate and the mixture is washed twice with water, dried and concentrated. The resulting diastereomer mixture is separated over a silica gel column using methylene chloride/ethyl acetate mixtures of 10:1 to 2:1, and the pure fractions are collected and concentrated. 1.25 g of the diastereomer A (R$_f$ value=0.27; TLC-aluroll, Merck, silica gel 60, F 254) and 778 mg of the crystalline deastereomer B of melting point: 274°-276° C. and R$_f$ value 0.20 are obtained.

PREPARATION EXAMPLES

Example 1

Ethyl (-)-2-amino-1,4-dihydropyridine-5-cyano-6-methyl-4-(3-phenylquinolin-5-yl)-3-carboxylate

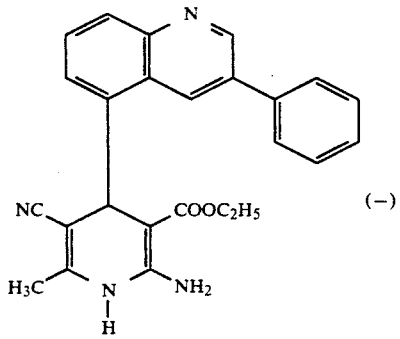

(−)

1.3 g (2.76 mmol) of the diastereomer B from Example 1 are added to a solution of 200 mg (28.3 mmol) of lithium in 25 ml of ethanol. The mixture is heated at the boiling point for 30 minutes, cooled and concentrated. The evaporation residue is taken up in ethyl acetate/water, the phases are separated and the organic phase is washed twice with water and concentrated. The resulting product is purified by flash chromatography and crystallised with acetonitrile. 678 mg of colourless crystals of melting point 195°–198° C. are obtained.

Example 3 (Process A)

Isopropyl 2-amino-1,4-dihydro-5-cyano-6-methyl-4-(3-phenyl-quinolin-5-yl)-pyridine-3-carboxylate

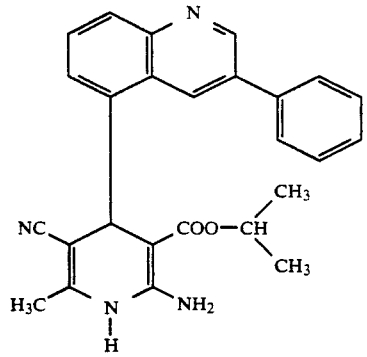

4.66 g (20 mmol) of 3-phenyl-quinoline-5-aldehyde are boiled in 40 ml of isopropanol with 1.64 g (20 mmol) of 3-aminocrotononitrile, 3.6 g (20 mmol) of isopropyl amidinoacetate hydrochloride and 1.64 g (20 mmol) of sodium acetate for 20 hours. The mixture is concentrated, the residue is taken up in ethyl acetate/water and the phases are separated. The organic phase is washed twice with water, dried and concentrated. The reaction mixture is separated over a silica gel column using methylene chloride/ethyl acetate mixtures. The desired fractions are collected and concentrated. The resulting evaporation residue is crystallised with acetonitrile and filtered off with suction 635 mg of colourless crystals of melting point 227°–229° C. are obtained.

Example 4

Isopropyl 2-amino-1,4-dihypropyridine-5-cyano-6-methyl-4-(3-(3-chlorophenyl)-quinolin-5-yl)-carboxylate

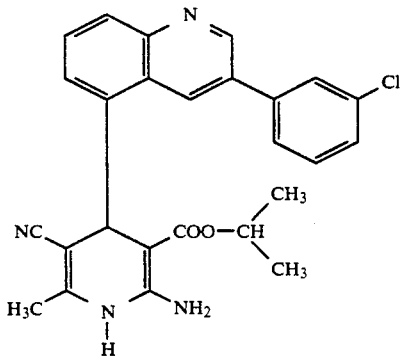

1.66 g (5 mmol) of 1-[3-(3-chlorophenyl)-quinol-5-ylidene]-3-oxo-butyro-nitrile are heated under reflux overnight in 10 ml of isopropanol with 905 mg (5 mmol) of isopropyl amidinoacetate hydrochloride and 410 mg (5 mmol) of sodium acetate. The mixture is cooled and concentrated. The resulting evaporation residue is dissolved in ethyl acetate/water, the phases are separated and the organic phase is washed with sodium bicarbonate solution and twice with water, dried and concentrated. Colourless crystals of melting point 264°–265° C. are obtained by stirring with acetonitrile.

Example 5- (Process B Without Isolation of the Intermediate Product)

n-Propyl 2-amino-1,4-dihydro-5-cyano-6-methyl-4-(3-phenyl-quinolin-5-yl)-pyridine-3-carboxylate

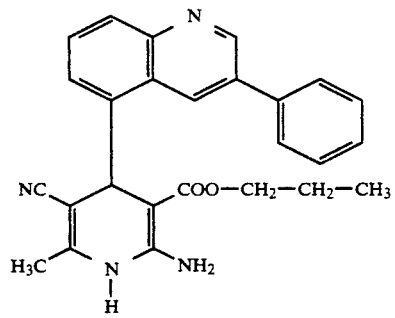

23.3 g (100 mmol) of 3-phenyl-quinoline-5-aldehyde are suspended in 200 ml of n-propanol and the suspension is stirred with 8.25 ml (100 mmol) of 5-methylisoxazole. A solution of 2.3 g of sodium in 100 ml of n-propanol is added dropwise and the mixture is stirred at 40°–50° C. for hours. A brown solution is obtained by this procedure. 8.04 g (100 mmol) of propyl amidinoacetate hydrochloride and 6 ml of acetic acid (100 mmol) are added and the mixture is boiled for 20 hours. It is concentrated, the residue is dissolved in ethyl acetate/water and the phases are separated. The ethyl acetate phase is washed with sodium bicarbonate solution and twice with water, dried and concentrated. The resulting residue is dissolved in 100 ml of hot acetonitrile and the product is left to crystallise. It is filtered off with suction and recrystallised from n-propanol and then from acetonitrile. 6.9 g of colourless crystals of melting point 237° C. are obtained.

The examples listed in Table 1 are prepared analogously to the instructions of Examples 1–5:

TABLE 1

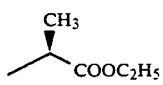

| Example No. | R¹ | R² | Melting point °C. | Enantiomer |
|---|---|---|---|---|
| 6 | H | —$C_2H_5$ | 174–77 | |
| 7 | H | —$CH_3$ | 230 | |
| 8 | 4-F | —$C_2H_5$ | 186–88 | |
| 9 | 4-F | -n-$C_3H_7$ | 226–28 | |
| 10 | 4-F | —$CH_3$ | 214–16 | |
| 11 | 4-F | —$CH(CH_3)_2$ | 226–28 | |
| 12 | H | —$CH_2$—$CH_2$—O—$CH_3$ | 248 | |
| 13 | H | n-$C_3H_7$ | 191–92 | (—) |
| 14 | H | —$CH(CH_3)_2$ | 263–65 | (—) |
| 15 | H | $\begin{array}{c}CH_3\\ \diagdown\\ COOC_2H_5\end{array}$ | 262 | (—) |
| 16 | 3-F | n-$C_3H_7$ | 219 | |
| 17 | 3-F | —$C_2H_5$ | 248 | |
| 18 | H | —$CH(CH_3)$—$CH_2$—$CH_3$ | Foam | (—) |
| 19 | H | —$CH_3$ | 262 | (—) |
| 20 | H | -n-$C_4H_9$ | 188 | (—) |
| 21 | H | n-$C_5H_{11}$ | 120 | (—) |
| 22 | H | $\begin{array}{c}CH_3\\ \diagdown\\ COO-CH(CH_3)_2\end{array}$ | 211–12 | |
| 23 | 4-$OCH_3$ | —$CH(CH_3)_2$ | 264 | |
| 24 | 3-F | —$CH(CH_3)_2$ | 204–06 | |

The examples listed in Table 2 are prepared analogously to the instruction of Example 1:

TABLE 2

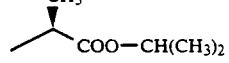

| Example No. | R² | Melting point °C. |
|---|---|---|
| 25 | -n-$C_3H_7$ | 173–76 |
| 26 | —$CH_3$ | 186–89 |

The examples listed in Table 3 are prepared analogously to the instructions of Examples 1 to 5:

TABLE 3

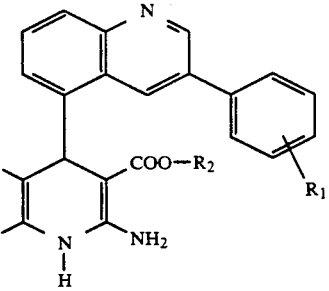

| Example No. | R¹ | R² | Melting point °C. | Enantiomer |
|---|---|---|---|---|
| 27 | H | —$CH(CH_3)_2$ | 204 (hydrochloride) | |
| 28 | 2-F | —$CH(CH_3)_2$ | 234 | |
| 29 | 2-F | —$CH_2$—$CH_2$—$CH_3$ | 204–5 | |
| 30 | 4-F | -n$C_3H_7$ | 217–19 | (—) |
| 31 | 4-F | —$CH(CH_3)_2$ | 270–71 | (—) |
| 32 | H | —$(CH_2)_2$—$OC_2H_5$ | 189 | (—) |
| 33 | H | —$CH_2$—$CH(CH_3)_2$ | 197 | (—) |
| 34 | H | —$CH_2$—$CH_2$—$C_6H_5$ | 145 | (—) |
| 35 | H | —$CH_2$—$C_6H_5$ | 225 | (—) |
| 36 | H | 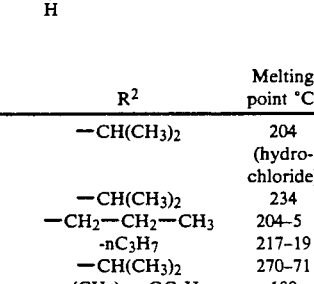 | 225 | (—) |
| 37 | H | —$(CH_2)_2$—O—$C_6H_5$ | 150 (decomposition) | (—) |
| 38 | H | —$(CH_2)_2$—O—$CH_3$ | 155 | (—) |
| 39 | H | —$(CH_2)_2$—OH | 179 | (—) |
| 40 | 3-$NO_2$ | —$(CH_2)_2$—$CH_3$ | 183 | |
| 41 | 3-$NO_2$ | —$CH(CH_3)_2$ | 248 | |
| 42 | H | 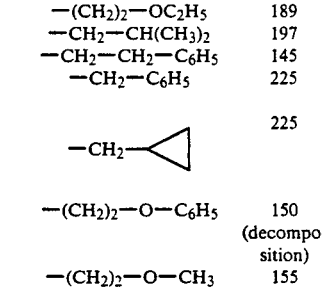 | Foam | (—) |
| 43 | H | 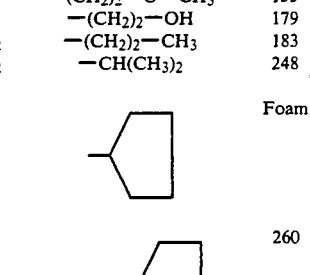 | 260 | (—) |
| 44 | 2-$CF_3$ | —$CH(CH_3)_2$ | 212 | |
| 45 | 2-$CF_3$ | n-$C_3H_7$ | 182 | |
| 46 | 3,4-$OCH_3$ | —$CH(CH_3)_2$ | 264 | |

We claim:
1. 2-Amino-5-cyano-4-quinoline-1,4-dihydropyridines of the general formula (I)

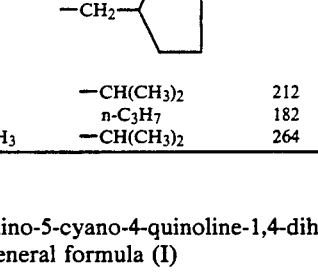
(I)

in which

R¹ represents aryl having 6 to 10 carbon atoms, which is optionally substituted up to 3 times, in an identical or different manner, by halogen, nitro, cyano, trifluoromethyl, trifluoromethoxy or trifluoromethylthio, or by straight-chain or branched alkyl having up to 8 carbon atoms, which can in turn be substituted by aryl having 6 to 10 carbon atoms, or is substituted by straight-chain or branched alkoxy or alkoxycarbonyl having in each case up to 8 carbon atoms, carboxyl or amino, or by a group of the formula —$NR^4R^5$, wherein $R^4$ and $R^5$ are identical or different and denote straight-chain or branched alkyl having up to 8 carbon atoms, phenyl or benzyl, or represents thienyl, R² represents hydrogen, or represents cycloalkyl having 5 to 8 carbon atoms, or represents straight-chain or branched alkyl, alkenyl, alkadienyl or alkinyl having in each case up to 10 carbon atoms, which are optionally substituted once or twice, in an identical or different manner, by halogen, hydroxyl, carboxyl, cyano or nitro, or by straight-chain or branched alkylthio, alkoxy, alkoxycarbonyl, acyl or acyloxy having in each case up to 8 carbon atoms, or cycloalkyl having 3 to 8 carbon atoms, or by phenoxy or phenyl, it being possible for the latter in turn to be substituted up to twice, in an identical or different manner, by halogen or by straight-chain or branched alkyl or alkoxy having in each case up to 6 carbon atoms, or are substituted by the group —$NR^4R^5$, wherein $R^4$ and $R^5$ have the abovementioned meaning, and R³ represents hydrogen or straight-chain or branched alkyl having up to 8 carbon atoms, and physiologically acceptable salts thereof.

2. Compounds of the general formula (I) according to claim 1, in which

R¹ represents phenyl, which is optionally substituted up to 3 times, in an identical or different manner, by halogen, nitro, cyano or trifluoromethyl, or by straight-chain or branched alkyl or alkoxy having in each case up to 6 carbon atoms, benzyl or by a group of the formula —$NR^4R^5$, wherein $R^4$ and $R^5$ are identical or different and denote hydrogen, straight-chain or branched alkyl having up to 6 carbon atoms, phenyl or benzyl, or represents thienyl, R² represents hydrogen, or represents cyclopentyl or cyclohexyl, or represents straight-chain or branched alkyl or alkenyl having in each case up to 10 carbon atoms, which are optionally substituted by halogen, hydroxyl, carboxyl or cyano, or by straight-chain or branched alkylthio, alkoxycarbonyl, alkoxy, acyl or acyloxy having in each case up to 6 carbon atoms, cyclopropyl, cyclopentyl, cyclohexyl, phenoxy or phenyl, it being possible for the last two to be substituted by halogen, methyl, methoxy or ethoxy, or are substituted by the group —$NR^4R^5$, wherein $R^4$ and $R^5$ have the abovementioned meaning, and R³ represents hydrogen or straight-chain or branched alkyl having up to 6 carbon atoms, and physiologically acceptable salts thereof.

3. Compounds of the general formula (I) according to claim 1, in which

R¹ represents phenyl, which is optionally substituted up to twice, in an identical or different manner, by fluorine, chlorine, nitro or trifluoromethyl, or by straight-chain or branched alkyl or alkoxy having in each case up to 4 carbon atoms, or by a group of the formula —$NR^4R^5$, wherein $R^4$ and $R^5$ are identical or different and denote hydrogen or straight-chain or branched alkyl having up to 4 carbon atoms, phenyl or benzyl, or represents thienyl, R² represents hydrogen, or represents cyclopentyl, or represents straight-chain or branched alkyl having up to 8 carbon atoms, which is optionally substituted by fluorine, chlorine, hydroxyl, carboxyl or cyano, or by straight-chain or branched alkoxycarbonyl, alkoxy or acyloxy having in each case up to 4 carbon atoms, phenyl, phenoxy, cyclopropyl, cyclopentyl or cyclohexyl, or by the group —$NR^4R^5$, wherein $R^4$ and $R^5$ have the abovementioned meaning, and R³ represents hydrogen, or represents straight-chain or branched alkyl having up to 4 carbon atoms, and physiologically acceptable salts thereof.

4. Medicament compositions containing at least one compound of the general formula (I) according to claim 1 and pharmaceutical auxiliaries and excipients therefor.

5. A method for treating cardiovascular disease in a patient in need thereof comprising administering to said patient an effective amount of a compound according to claim 1.

6. 2-amino-5-cyano-4-quinoline-1,4-dihydropyridine of the formula

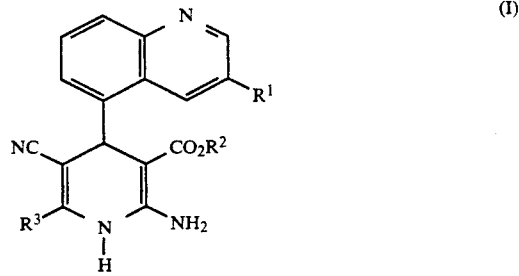

wherein R¹ is hydrogen, R² is n-$C_3H_7$, and R₃ is methyl.

7. 2-amino-5-cyano-4-quinoline-1,4-dihydropyridine of the formula

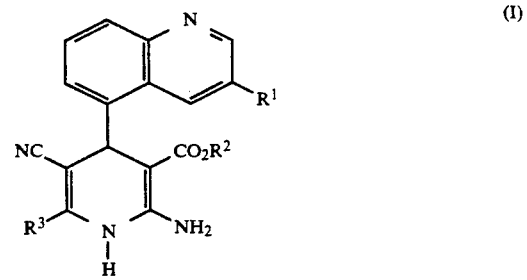

wherein R¹ hydrogen, R² is —$CH(CH_3)_2$, and R₃ is methyl.

* * * * *

UNITED STATES PATENT AND TRADEMARK OFFICE
CERTIFICATE OF CORRECTION

PATENT NO. : 5,225,558
DATED : July 6, 1993
INVENTOR(S) : Stoltefuss et al.

It is certified that error appears in the above-indentified patent and that said Letters Patent is hereby corrected as shown below:

Col. 8, line 57  Delete "acetate" and substitute --propionate--.

Signed and Sealed this

Eleventh Day of July, 1995

Attest:

BRUCE LEHMAN

Attesting Officer  Commissioner of Patents and Trademarks